US00PP19530P2

(12) United States Plant Patent
Bradford

(10) Patent No.: US PP19,530 P2
(45) Date of Patent: Dec. 2, 2008

(54) INTERSPECIFIC TREE NAMED 'PLUMSWEET XIII'

(50) Latin Name: ***Prunus* sp.**
Varietal Denomination: Plumsweet XIII

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/984,895

(22) Filed: Nov. 26, 2007

(51) Int. Cl.
*A01H 5/00* (2006.01)

(52) U.S. Cl. ..... Plt./180

(58) Field of Classification Search ..... Plt./180
See application file for complete search history.

(56) References Cited

U.S. PATENT DOCUMENTS

PP15,809 P2 6/2005 Bradford
PP16,461 P2 4/2006 Bradford

*Primary Examiner*—Annette H Para
*Assistant Examiner*—S. B. McCormick-Ewoldt

(57) ABSTRACT

The present invention relates to an interspecific tree and more particularly to a new and distinct variety broadly characterized by a medium size, vigorous, hardy, and somewhat productive tree. The variety is self-unfruitful, blooms in the early season, and produces an abundance of blossoms and pollen. The fruit matures under the ecological conditions described during mid July, with first picking on Jul. 11, 2007, and will hang on the tree for about fifteen more days. The fruit is uniformly large in size, red mottled over a yellow background in skin color, clingstone in type, oblate in shape, red and orange yellow in flesh color, very firm and crisp in texture, and excellent in flavor.

1 Drawing Sheet

Botanical classification: *Prunus* sp.
Varietal denomination: 'Plumsweet XIII'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Plumsweet XIII'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2001 one tree of 'YUMMY® gem' (U.S. Plant Pat. No. 15,809) plum was crossed by me in this manner. To pollinate this isolated tree, I selected bouquets from several sources of apricot and interspecific plum-apricot hybrid trees without keeping specific written details. Upon reaching maturity the fruit from this plum tree was harvested and the seeds were removed, cracked, stratified and germinated as a group with the label "H10P881". They were grown as seedlings on their own root in my greenhouse and upon reaching dormancy transplanted to a cultivated area of my experimental orchard located near Le Grand, Calif. in Merced County (San Joaquin Valley). During the summer of 2004 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed patent, 'YUMMY® gem' (U.S. Plant Pat. No. 15,809) plum by being self-unfruitful and producing fruit that is sweet and excellent in flavor, but is quite distinguished therefrom by producing fruit that is larger in size, that is mottled in skin color, that matures about forty-three days later, and that is partially red in flesh color instead of yellow.

The present variety is more similar to 'Plumsweet IV' (U.S. Plant Pat. No. 16,461) interspecific tree by being self-unfruitful and by producing fruit that is mottled in skin color, partially red in flesh color, and excellent in flavor, but is distinguished therefrom by blooming in the early season instead of mid season and by producing fruit that is oblate instead of oblong in shape, that has a less pronounced suture, and that matures about fifty days earlier.

SUMMARY OF VARIETY

The present interspecific variety is characterized by a medium size, vigorous, hardy, and somewhat productive tree. Being self-unfruitful, the present variety requires cross pollination from an apricot, interspecific, or plum that blooms during the early season. The present variety's abundance of blossoms and pollen entices strong bee activity to facilitate pollination. The fruit matures under the ecological conditions described during mid July, with first picking on Jul. 11, 2007, and will hang on the tree for about fifteen more days. The fruit is uniformly large in size, red mottled over a yellow background in skin color, clingstone in type, oblate in shape, red and orange yellow in flesh color, very firm and crisp in texture, and excellent in flavor.

DRAWING

The accompanying photograph consists of four whole fruits positioned to display the characteristics of the skin color and form, a half fruit divided to reveal the flesh and stone, typical leaves, a tip shoot growth, and an inset depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of full ripe on Jul. 23, 2007, on the original tree during its sixth growing season. The flower and bud descriptions were developed during the previous blooming season. All major color code designations are by reference to the Inter-Society Color Council, National Bureau of Standards. Common color names are also used occasionally.

Parentage

Seed parent: 'YUMMY® gem' plum (U.S. Plant Pat. No. 15,809).

Pollen parent: Unknown.

Tree

Size: Medium, reaching and maintaining a height of 10' [3.05 m.] and a spread of 8' [2.44 m.] after six growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable early seasonal blooming apricot, interspecific, or plum, such as 'Yummygem' (U.S. Plant Pat. No. 15,809).

Bearing: Uncertain bearer, weather dependent.

Trunk:

*Size.*—Large, reaching a maxium diameter of 4½" [114 mm.] after the sixth growing season.

*Texture.*—Shaggy.

*Bark color.*—A Deep yellowish brown [75. deep yBr] and Deep brown [56. deep Br] variegation with Grayish yellowish brown [80. gy.yBr] crevices present.

*Lenticels.*—Approximate Number Per Square Inch: 10. Color: Moderate yellowish brown [77. m.yBr]. Average Size: ¼" [6.4 mm.]. Shape: Eye-shaped, elongated.

Branches:

*Size.*—Diameter of limb is 2" [51 mm.] measured 12" above the crotch, 1" [25 mm.] measured 12" above the first fork.

*Texture.*—Smooth on first and second year wood, increasing roughness with age.

*Color.*—1st Year Wood Topside: Deep yellowish brown [75. deep yBr]. 1st Year Wood Underside: Moderate yellow green [120. m.YG]. Older Wood: A Deep yellowish brown [75. deep yBr] and Dark yellowish brown [78. d.yBr] variegation.

*Lenticels.*—Number Per Square Inch: More than 60 on second year wood. Color: Dark orange yellow [72. d.OY]. Average Size: 1/64" [0.4 mm.]. Shape: Elongated, rectangular.

Leaves:

*Size.*—Medium. Average Length: 3⅝" [92 mm.]. Average width: 1⅞" [48 mm.].

*Arrangement.*—Alternate.

*Thickness.*—Medium.

*Form.*—Elliptical.

*Apex.*—Acuminate.

*Base.*—Some rounded, some acute with an average angle base angle of 80 degrees.

*Surface.*—Smooth.

*Color.*—Dorsal Surface: Moderate olive green [125. m.OlG]. Ventral Surface: Grayish yellow green [122. gy.YG].

*Margin.*—Finely serrate.

*Venation.*—Pinnately net veined.

*Petiole.*—Average Length: ½" [12.7 mm.]. Average Thickness: 1/16" [1.6 mm.]. Color: Light yellow green [119. l.YG].

*Stipules.*—Number: 2 per leaf, up to 6 per growing tip. Average Length: 7/16" [11.1 mm.]. Color: Brilliant yellow green [116. brill.YG] becoming Moderate reddish brown [43. m.rBr] with age.

*Glands.*—Number: Mostly 2 per leaf. Position: Alternately positioned at petiole and base of leaf blade. Size: Small. Form: Globose. Color: Strong yellow green [117. s.YG] becoming Deep reddish brown [41. deep rBr] with age. Leaf buds: Pointed, medium.

Flower buds:

*Hardiness.*—Hardy, with respect to central California winters.

*Diameter.*—Typically 3/16" [4.8 mm.] 1 week before bloom.

*Length.*—Typically ⅜" [9.5 mm.] 1 week before bloom.

*Form.*—Not appressed.

*Surface.*—Pubescent.

*Tip color.*—White [263. White].

Flowers: Perfect, complete, perigynous, usually a single pistil, typically thirty or more stamens, five sepals and petal locations alternately positioned.

*Average flower diameter.*—15/16" [23.8 mm.].

*Number of petals.*—Five, no double blossoms observed.

*Petal shape.*—Oval to circular.

*Petal margin.*—Entire, somewhat wavy with notches typical.

*Average petal diameter.*—7/16" [11.1 mm.].

*Average petal length.*—½" [12.7 mm.].

*Petal apex.*—Rounded.

*Petal base.*—Obtuse.

*Petal color.*—White [263. White] on both sides.

*Anther color.*—Very yellow [82. v.Y].

*Stigma color.*—Brilliant greenish yellow [98. brill.gY].

*Sepal color.*—Brilliant yellow green [116. brill.YG].

*Sepal length.*—⅛" [3.2 mm.].

*Sepal width.*—⅛" [3.2 mm.].
*Sepal apex.*—Rounded to elliptical to match the width and length.
*Sepal margin.*—Fairly smooth to the naked eye, slightly serrate when magnified.
*Average pistil length.*—11/16" [17.5 mm.], longer than normal.
*Average stamen length.*—½" [12.7 mm.].
*Fragrance.*—Moderate.
*Pollen production.*—Abundant, very bee enticing.
*Blooming period.*—Early, five days before 'Ambra' (unpatented).
*Onset of bloom.*—One percent on Feb. 17, 2007.
*Date of full bloom.*—Mar. 3, 2007.
*Duration of bloom.*—One to two weeks, dependent on ambient temperature.
*Bloom density.*—Heavy.
*Number per cluster.*—2 to 10, average 4.

FRUIT

Maturity when described: Full ripe, Jul. 23, 2007.
Date of first picking: Jul. 11, 2007.
Date of last picking: Jul. 25, 2007.
Size: Uniform, Medium.
*Average diameter axially.*—2¼" [57.2 mm.].
*Average diameter across cheek plane.*—2⅝" [66.7 mm.].
*Average diameter across suture plane.*—2½" [63.5 mm.].
*Typical weight.*—5.5 ounces [156 grams].
Form: Uniform, oblate, symmetrical.
*Longitudinal section form.*—Oblate to elliptical.
*Transverse section through diameter.*—Round.
Suture: A distinct line located in a very shallow groove extending from the base to just beyond the apex, ending in a small depression.
Ventral surface: Rounded.
Lips: Virtually no lipping.
Cavity: Flaring, circular, suture showing on one side.
*Depth.*—⅜" [9.5 mm.].
*Breadth.*—13/16" [20.6 mm.].
Base: Truncate.
Apex: Truncate.
Pistil point: An inconspicuous dot.
Stem: Medium.
*Average length.*—⅜" [9.5 mm.].
*Average width.*—5/64" [2.0 mm.].
Skin:
*Thickness.*—Medium.
*Surface.*—Smooth.
*Tenacity.*—Tenacious to the flesh.
*Astringency.*—Slight.
*Tendency to crack.*—Very slight.
*Color.*—Deep red [13. deep R] mottled over a Moderate yellow [87. m.Y] background with Dark greenish yellow [103. d.gY] freckling throughout.
*Bloom.*—Abundant.
Flesh:
*Color.*—Light orange yellow [70. l.OY] toward the stone smoothly blending into Deep red [13. deep R] near the skin.
*Surface of pit cavity.*—Covered with Moderate orange yellow [71. m.OY] broken fibers when twisted from the stone.
*Amygdalin.*—Moderate.
*Juice.*—Moderate, rich.
*Texture.*—Firm, crisp.
*Fibers.*—Abundant, fine, tender.
*Ripens.*—Slightly earlier toward the apex and along the suture.
*Flavor.*—A tasty blend of acid and sugar, typically 20 brix.
*Aroma.*—Moderate.
*Eating quality.*—Very good.

STONE

Type: Clingstone.
Form: Oval.
Hilum: Narrow.
Base: Straight.
Apex: Acuminate, with a sharp 1/16" [1.6 mm.] tip.
Sides: Equal.
Surface: Rough throughout with a deep groove from base to apex on each side of the dorsal fin.
External color of stone: Strong yellowish brown [74. s.yBr].
Pit wall color when cracked: Pale orange yellow [73. p.OY].
Cavity surface color: Moderate orange yellow [71. m.OY].
Average pit wall thickness: 1/16" [1.6 mm.].
Average width: 11/16" [17.5 mm.].
Average length: 13/16" [20.6 mm.].
Average breadth: ⅜" [9.5 mm.].
Tendency to split: None observed.
Kernel:
*Form.*—Oval.
*Skin color.*—Light yellow [86. l.Y] when first removed.
*Pellicle color.*—Light grayish yellowish brown [79. l.gy.yBr].
*Vein color.*—Light yellowish brown [76. l.yBr].
*Taste.*—Bitter.
*Viable.*—Yes.
*Average width.*—⅜" [9.5 mm.].
*Average length.*—½" [12.7 mm.].
*Amygdalin.*—Moderate.

Use

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'Plumsweet IV' (U.S. Plant Pat. No. 16,461) interspecific tree by being self-unfruitful and by producing fruit that is mottled in skin color, partially red in flesh color, and excellent in flavor, but is distinguished therefrom by blooming in the early season instead of mid season and by producing fruit that is oblate instead of oblong in shape, that has a less pronounced suture, and that matures about fifty days earlier.

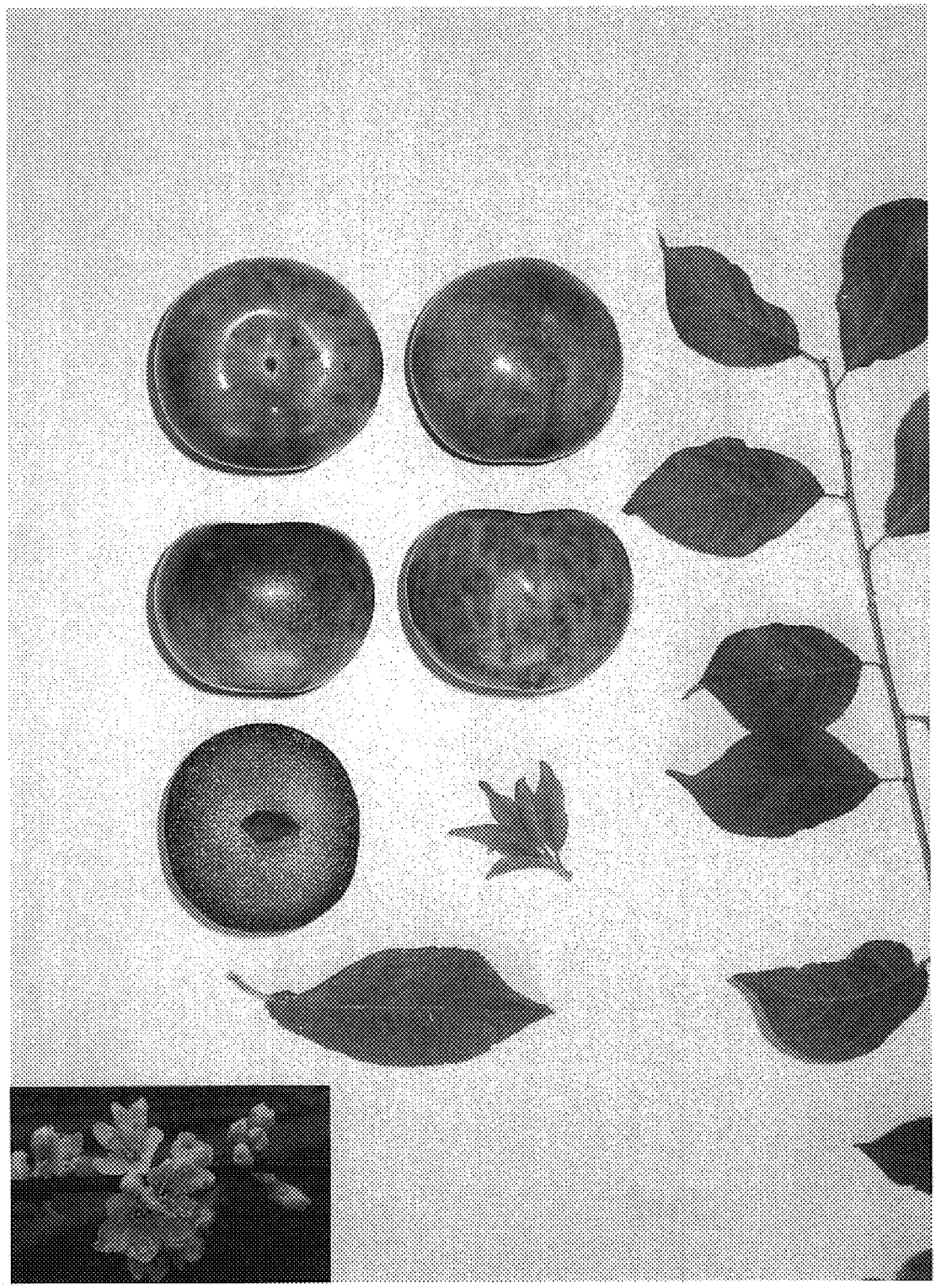

* * * * *